United States Patent
Watkins et al.

(12) 
(10) Patent No.: US 6,451,844 B1
(45) Date of Patent: Sep. 17, 2002

(54) USE OF MENTHYL-2 PYRROLIDONE-5-CARBOXYLATE AS AN INSECT REPELLENT

(75) Inventors: Stephen D Watkins; Maxine J Hills; Richard A Birch, all of Kent (GB)

(73) Assignee: Quest International BV, Naarden (NL)

( * ) Notice: Subject to any disclaimer, the term of this patent is extended or adjusted under 35 U.S.C. 154(b) by 0 days.

(21) Appl. No.: 09/787,320

(22) PCT Filed: Aug. 25, 1999

(86) PCT No.: PCT/GB99/02808
§ 371 (c)(1),
(2), (4) Date: Mar. 16, 2001

(87) PCT Pub. No.: WO00/16738
PCT Pub. Date: Mar. 30, 2000

(30) Foreign Application Priority Data

Sep. 18, 1998 (GB) ............................................. 9820233

(51) Int. Cl.$^7$ ........................ A01N 43/36; A01N 37/18; A01N 37/10; A01N 65/00; A61K 7/40
(52) U.S. Cl. ........................ 514/423; 514/425; 514/468; 514/470; 514/533; 514/617; 514/691; 514/692; 514/703; 514/718; 514/763; 514/919; 424/195.18; 424/742; 424/747; 424/750; 424/770; 424/DIG. 10
(58) Field of Search ................................ 514/919, 423, 514/425, 468, 470, 533, 617, 691, 692, 703, 718, 763; 424/DIG. 10, 195.18, 742, 747, 750, 770

(56) References Cited

U.S. PATENT DOCUMENTS 6,048,549 A * 4/2000 Nitikhunkasem et al. ... 424/489

FOREIGN PATENT DOCUMENTS

| BE | 723 816 | | 4/1969 |
| DE | 2 102 172 | | 7/1972 |
| DE | 2707814 | * | 9/1977 |
| GB | 1 567 496 | | 5/1980 |

OTHER PUBLICATIONS

Chemical Abstracts 87:189314, abstracting DE 2,707,814, 1977.*

Database WPI, Week 199515, Derwent Publication Ltd., London, GB; an 1995–110501 xp002123858 "Insecticide non-toxic to humans and animals—contains surfactant and water retaining space" & JP 07 033608 A (Japan Tobacco), Feb. 3, 1995, abstract.

Database WPI, Week198909 Derwent Publications Ltd., London, GB; AN 1989–064951 XP002123859 "Non-Toxic insecticide compsn.—contg. insect growth regulator and organic chlorine cpd., menthol, aldehyde, ketone, ether or pinene" & JP 01 016706 A (Mikasa Kagaku Kogyo), Jan. 20, 1989, abstract.

* cited by examiner

*Primary Examiner*—John Pak
(74) *Attorney, Agent, or Firm*—Morgan, Lewis & Bockius LLP

(57) ABSTRACT

The use of menthyl 2-pyrrolidone-5-carboxylate as an insect repellent, usually by application to a substrate or into an air space. The menthyl 2-pyrrolidone-5-arboxylate can be used as a composition, which may be perfumed. A useful composition comprises a mixture of menthyl 2-pyrrolidone-5-arboxylate and a known insect repellent or a compound shown to be an effective insect repellent on a test described herein.

15 Claims, 1 Drawing Sheet

US 6,451,844 B1

USE OF MENTHYL-2 PYRROLIDONE-5-CARBOXYLATE AS AN INSECT REPELLENT

This application is a 371 of PCT/GB99/02808, filed on Aug. 25, 1999.

FIELD OF INVENTION

The present invention relates to the use of a menthyl ester as an insect repellent, to compositions containing the menthyl ester and to a method of repelling insects.

BACKGROUND

Insects have long been known as a nuisance and, for some insect genera, as a health hazard. Mosquitoes, for instance, are a proven vector of diseases, and the genus Aedes in particular is associated with yellow fever, dengue, encephalitis and malaria (Encyclopaedia Britannica). Although the problems may be reduced at source with the use of DDT and other chemical sprays in the breeding areas, fears over the persistence of chlorchemicals combined with increasing mosquito resistance to control chemicals (e.g. insecticides) have led to a reappraisal of the magnitude of the nuisance and the hazard. Physical barriers to the insects are not always possible, e.g. in the open air, where some form of personal repellent is necessary.

It is also a feature of recent times that the more environmentally-aware public tend to question the safety of many chemicals which were formerly taken for granted. One of these is the well-known personal insect repellent N,N-diethyl-m-toluamide (abbreviated as DEET, and commercially available as Delphone ™. This was originally seen as the natural successor to the parent molecule, N,N-diethylbenzamide which was found to be strongly insect repellent but also irritating to human skin (McCabe et al., (1954), J. Org Chem. 19, 493–498). Fears over possible allergenicity, disclosed in European Patent Application No. 167266 (Angus Chemical Company), as well as aversion to some of the physical properties of this compound such as oiliness and odour, have led to the search for less hazardous and more aesthetically acceptable methods of repelling insect pests, particularly mosquitoes.

REVIEW OF THE PRIOR ART

Certain compounds have long been known to posses insect deterrent properties, some of this information coming from what might be termed"folk knowledge". These materials include widely-known substances such as Citronella, Tolu and Peru Balsams, Eucalyptus oils, Huon Pine and other similar oils [M. Bouvier, International Frag. Co-ord. Oct. 29, 1976]. Other materials known for their deterrent properties include those having camphoraceous odours, such as Camphor itself, Cypress oils, Galbanum etc. [H&R Contact, 36, 1984].

A more scientific approach to the properties of these natural sources has been undertaken by various researchers, such as Lemberkovics et al. [Acta Pharmaceutica Hungarica, 57, (1987) 133–142], Nahrstedt [Planta med. 42(4), 313–32 (1981)], and Popescu [Chim. Anal. (Bucharest), 2(1), 59–61 (1972)] who investigated the effects of Walnut Leaf oil. Kumbu and DiPhanzu [Plant Med. Phytother. 16(1), 23–6 (1975)] investigated the deterrent effect of a range of Eucalypts against a selection of insect pests.

The popularly-used DEET has also been studied in comparison, and in conjunction, with a range of ingredients by various researchers. Nishimura et al. [Kagaku to Seibbutsu, 27(8), 4886–6 (1989)] investigated the possible synergy of Eucalyptus citriodora and menthanediols with DEET. Solvents such as diethyl phthalate, dimethyl phthalate and dibutyl phthalate are also well known, and these provide the basis for commercial repellents which do not contain DEET, and are also cited in Kirk-Othmer Encyclopedia of Chemical Technology [3rd Edn., Vol. 13, 476ff]. Canadian patent 1 230 826 (1988) uses a combination of Citronela or Lavender oils, 2-ethylhexanediol and dimethyl phthalate.

Repellent chemicals may be classified into two main groups: general deterrents and species-specific deterrents. Substances known to deter one species have been known to serve as an attractant to another. An example of this is the use of a mixture of citronellol and eugenol against clothes moths and Anthrenus beetles, described in German patent application DE 3 901 341A [published 1990, Detia Freyberg GmbH]. The latter ingredient, Eugenol, is considered to be a general insect attractant [Kirk Othmer Encyclopedia of Chemical Technology, cited above]. DEET, however, is considered to be a general, or broad-spectrum, insect repellent. Materials potentially useful as insect repellents are frequently tested against mosquitoes, in particular against the genus Aedes. These materials may also act as general insect repellents.

PCT Application WO 96/08147 discloses the use of a number of different compounds as insect repellents and also a method by which the repellency of compounds to insects can be reliably tested. UK Patent GB 1 567 496 discloses a number of terpene esters of 2-pyrrolidone-5-carboxylic acid which are useful in anti-inflammatory topical compositions. These esters are effective as long lasting physiological coolants and their efficacy is believed to be due to enzymatic hydrolysis on skin that ensures a low level of hydrolysed terpene alcohol (e.g. menthol), which provides a coolant effect, and pyrrolidone carboxylic acid, a natural moisturising factor which conditions the skin.

SUMMARY OF THE INVENTION

It has now been surprisingly found that the menthyl ester of 2-pyrrolidone-5-carboxylic acid is an effective insect repellent under conditions in which the above-mentioned hydrolysis is not believed to occur. It has also been shown that the ester is a more effective insect repellent than its hydrolysis product, menthol, and the superior repellency is maintained for at least I hour after application to a substrate.

Consequently, the invention comprises the use of menthyl 2-pyrrolidone-5-carboxylate as an insect repellent.

Menthyl 2-pyrrolidone-5-carboxylate is commercially available under the Trade Mark QUESTICE but it has not heretofore been recognised as an insect repellent.

In another aspect, the invention provides a method of repelling insects from an object or an airspace, comprising application to the object or into the airspace, of an effective amount of menthyl 2-pyrrolidone-5-carboxylate. Typically the object is a human body.

The menthyl 2-pyrrolidone-5-carboxylate used as an insect repellent in accordance with the invention can be used in the form of a composition which contains components other than menthyl 2-pyrrolidone-5-carboxylate. In one embodiment, the composition is a perfumed composition.

Preferably, the menthyl 2-pyrrolidone-5-carboxylate composition defined above is used to repel biting insects, such as mosquitoes, particularly members of the genus Aedes.

The composition used in the invention, whether perfumed or not, preferably contains at least 0.05% by weight, more preferably at least 0.5% by weight, and most preferably at least 2.0% by weight of menthyl 2-pyrrolidone-5-carboxylate. Compositions containing not more than 10% by weight of menthyl 2-pyrrolidone-5-carboxylate have been shown to be effective insect repellent compositions.

Compositions used in accordance with the invention preferably constitute, or comprise, personal products or cosmetics for use on the skin and/or hair. Examples of such products include fine fragrances, colognes, skin creams, skin lotions, deodorants, talcs, bath oils, soaps, shampoos, hair conditioners and styling agents.

Alternatively, compositions used in accordance with the invention may constitute, or be comprised in, household products such as: air fresheners (including"heated" air fresheners in which insect repellent substances are released upon heating e.g. electrically, or by burning [e.g. joss-sticks, candles]), hard surface cleaners or laundry products (e.g. laundry detergent-containing compositions and conditioners).

Preferably the cosmetics, personal products and household products defined above comprise between 0.1% and 10% of a composition used in accordance with the invention.

The compositions used in the invention may comprise additional materials to produce desired products such as pleasing perfumes with useful repellent activity. Other materials which may be present in the compositions (at concentrations from 0 to 99.95% by weight) include fragrances, solvents, diluents and fixatives known in the art, such as: Aldehyde C11 (Undecylenic Aldehyde); Aldehyde iso C11 (GIV); Allspice oil; Allyl cyclohexyl propionate; Amyl salicylate; Amylcinnamic aldehyde; Anethole; Anisic alcohol; Anisic aldehyde; Applinal (Q); Bay oil; Benzyl acetate; Benzyl benzoate; Benzyl cinnamate; Benzyl propionate; Benzyl salicylate; Bourgeonal (Q); Brahmanol; Camphor powder synthetic; Cedarwood Virginion; Cedrenol; Cedryl acetate; Celestolide (IFF); Cineole; Cinnamic alcohol; cinnamic aldehyde; Cinnamon Leaf Oil; Cinnamyl acetate; cis-3-Hexenol; Citral; Citronella oil; Citronellal; Citronellol; Citronellyl acetate; Citronellyl oxyacetaidehyde; Clove oil; Coriander oil; Coumarin; Cuinic aldehyde; Cyclamen aldehyde; Decanal; 9-Decenol; Dibenzyl ether; Dibutyl phthalate; Diethyl Phthalate; Dihydromyrcenol; Dimethyl anthranilate; Dimethyl phthalate; Dimycretol (IFF); diphenylmethane; Diphenyl oxide; Dimethyl benzyl carbinyl acetate; Dodecanol; Dodecanal; Elemi oil; Ethyl methyl phenyl glycidate; Ethyl cinnamate; Ethyl safranate (Q); ethyl vanillin; Eugenol; Evergreen oils (Pine oils etc.); gamma-Nonalactone; gamma-undecalactone; Cardamide (Q); Geraniol; Geranium bourbon; Geranyl acetate; Geranyl formate; Gum Benzoin; Heliotropin; Hercolyn D (HER); Hexyl benzoate; Hexylcinnamic aldehyde; Hydratropic aldehyde dimethyl acetal; Hydroxycitronellal; Hydroxycitronellal dimethyl acetal; Indole; iso Bornyl acetate; Iso-longifolanone; Isopropyl myristate; Iso-cyclocitral (GIV, IFF); Jasmacyclene; Jasmin oil; Lavandin Abrialis; Lavender oil; Lilial (GIV); Linalol; Linalyl acetate; Maceal (0); Menthol Laevo; Methyl anthranilate; Methyl cedryl ketone; Methyl dihydrojasmonate; Methyl ionone; Methyl ionone alpha iso; Methyl myristate; Methyl naphthyl ketone; Methyl salicylate; Moss treemoss; Musk ketone; Neocaspirene (Q); Nerol; Nerolin Bromelia; Neryl acetate; Nonanal; Oakmoss absolute; Octanol Olibanum resinoid; para-Cresyl phenylacetate; para-Methoxyacetophenone; Patchouli oil; Peppermint oil; Petitgrain oil; 2-Phenoxyethanol; Phenoxyethyl iso butyrate; Phenylethylacetate; Phenyethyl alcohol; Phenylethyl butyrate; Phenylethyl phenylacetate; Pimento oil; Pinene, alpha; Para-tert. butyl-cyclohexyl acetate; Resinoid Benzoin Siam; Rose oil; Rosemary oil; Sandalwood oil; terpineol; Tetrahydrolinalol; Tetrahydromuguol (IFF); Thyme Red; Undecanal; Vanillin; Verbena oil; Vetyvert Bourbon; Yara and Ylang ylang.

Compounds are obtainable from the suppliers as indicated below: for those compounds labelled"(Q)"—Quest International,"(IFF)"—International Flavours & Fragrances, Inc., "(GIV)"—Givaudan,"(HER)"—Hercules B.V.

Other active and non-active materials may be present, such as:

acidic mucopolysaccharides and their salts, Aesculus hipocastanum, aloe barbadenisis Mil (Aloe Vera Linne), α-hydroxycarboxylic acids, α-ketocarboxylic acids, amide derivatives, amino acids, amphiphilic cyclodextrin derivatives, β-sitosterol, carboxy vinyl polymer water soluble salts, carboxymethyl cellulose, carrageenan, chitin, chitosan, cholesterol, cholesterol fatty acid ester, collagen, dicarboxylic acid monostearyl esters, di-fatty acid glycerol esters, digalactosyl diglyceride, ersterol, ethanol, extract of Swertia japonica Makino, fatty acids, fatty acid citrate esters, fatty alcohols, ginseng extract, glucose esters of higher fatty acids, guar gum, gum arabic, Hamamelidaceae (Hamamelis Virginiana Witch hazel), hyaluronic acid, hydrochyloesterol, hydroxybenzoic acids, isomaltose, isopropyl alcohol, lactose, lanosterol, lipids extracted from the biomass of microorganisms, yeasts, moulds and bacteria, liposomes, locust bean gum, low molecular acidic mucopolysaccharides and their salts, low molecular weight humectant components, maltose, mineral oils, mineral powders, monocisalkenoic acid, mucopolysaccharides, mycosterol, N-acyl lysines, N-isostearyl lysine, N-lauroyl lysine, N-myristyl lysine, N-palmitoyl lysine, N-stearoyl lysine, natrium type bentonite, natural or synthetic aminoacid with protein or peptide bonds, NMF ingredients, nonvolatile silicones, oil agents, oil matter, oligosaccharides, organic acids, pantothenic acid and its derivatives, petroleum jelly, phosphatidyl ethanolamine, phosphatidylcholine, phospholipids, polysaccharides, polyvinyl alcohol, polypeptides, proteins, raffinose, saponins, sodium hyaluronate, sources of linoleic acid, sterols, sterol esters, stigmasterol, sucrose, sugar esters of higher fatty acids, sulphatide, sunscreens, surfactants, talc, thymosterol, tocopherol, mono-, di- or tri-glycerides, vitamins and analogues, vitamin E and/or its ester compounds, volatile silicone fluids, water-soluble moisture-retaining agents, water-soluble polymers and waxes.

Menthyl 2-pyrrolidone-5-carboxylate can be used as the sole insect repellent in a composition or may be used in combination with other compounds which are effective insect repellents.

A further aspect of the invention comprises a mixture of menthyl 2-pyrrolidone-5-carboxylate with a known insect repellent. Known insect repellents which are suitable for use in a mixture with menthyl 2-pyrrolidone-5-carboxylate include N,N-diethyl-m-toluamide (DEET); N,N-diethylbenzamide; citronella; Tolu balsam; Peru balsam; Eucalyptus oil; Huon pine oil; camphor; cypress oil; galbanum; diethyl phthalate; dimethyl phthalate; dibutyl phthalate; 1,2,3a,4,5,5a,6,7,8,9,9a,9b-dodecahydro-3a,6,6,9a-tetra-methyinaphtho[2,1-b] furan; 4-(tricyclo [5.2.1 .0$^{2,6}$] decylidene-8) butanal; 1-ethoxy-1(2'-phenylethoxy)ethane; acetyl cedrene and propylidene phthalide.

A composition according to the invention also comprises a mixture of menthyl 2-pyrrolidone-5-carboxylate and a second compound, said second compound having a repellency of at least 20% as determined by the insect repellency test defined in Example 1. Preferably, the second compound has a repellency of at least 40%, more preferably at least 50%, according to said test.

A further composition according to the invention comprises a mixture of menthyl 2-pyrrolidone-5-carboxylate and a second compound, said second compound being present in an amount which is sufficient to ensure that said second compound contributes to said composition an insect repellent effect equivalent to a repellency of at least 10% as. determined by the insect repellency test defined in Example 1. Preferably, the second compound is present in said composition in an amount which is sufficient to ensure that said second compound contributes an insect repellent effect equivalent to a repellency of at least 20% as determined by said insect repellency test. More preferably, the insect repellent effect contributed by the second compound is equivalent to a repellency of at least 30%.

BRIEF DESCRIPTION OF THE DRAWING

The invention is illustrated by the following non-limiting examples and by reference to FIG. 1 which is a schematic representation of an apparatus suitable for testing compounds as insect repellents.

EXAMPLE 1

Insect Repellency Test

Figure 1:
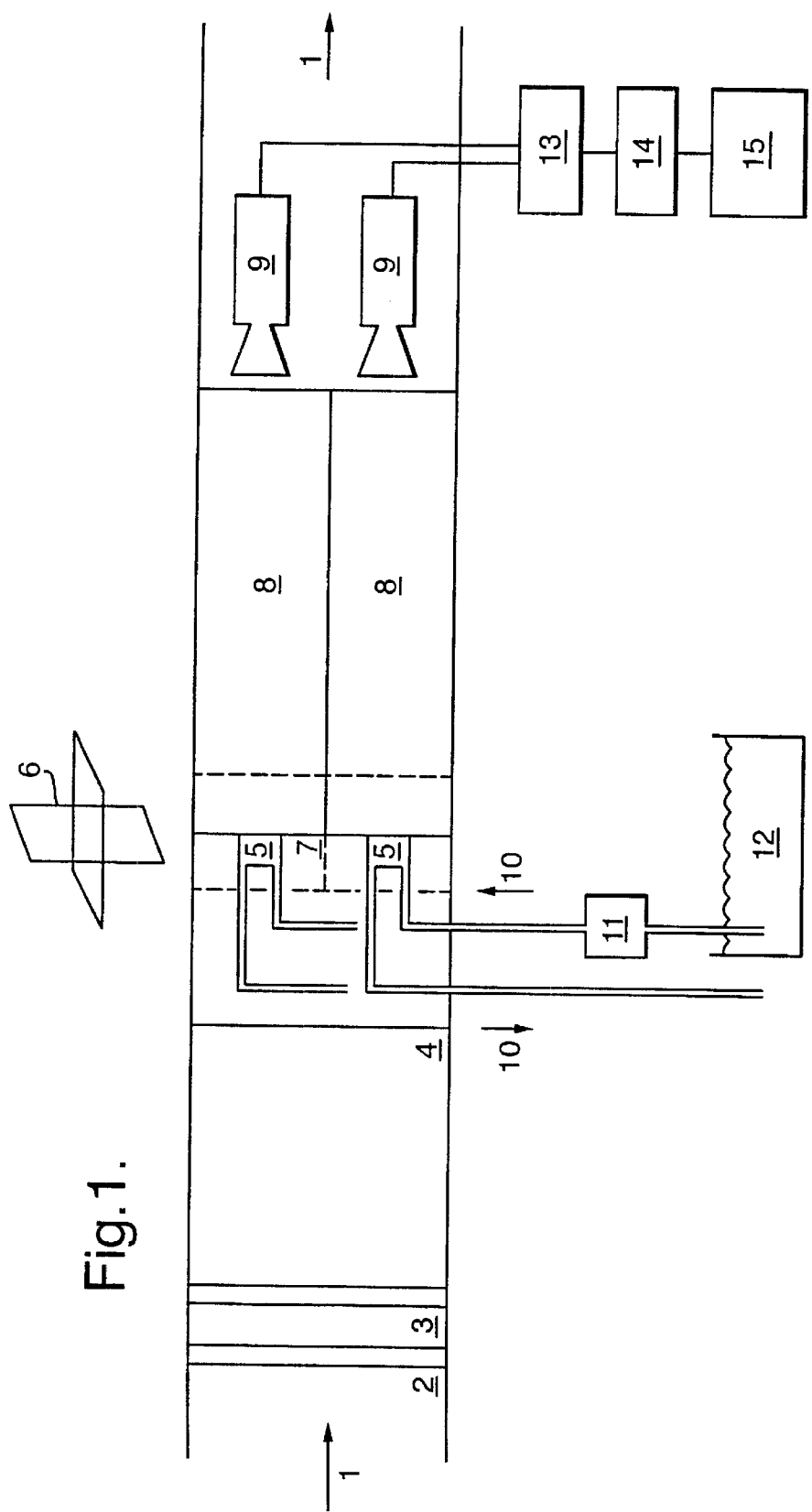

The effectiveness of menthyl 2-pyrrolidone-5-carboxylate as an insect repellent was tested using an apparatus similar to that disclosed in PCT Application WO 96/08147 and illustrated in FIG. 1. The method is described for testing of menthyl 2-pyrrolidone-5-carboxylate but can be adapted to test any other compound in place of menthyl 2-pyrrolidone-5-carboxylate.

Four test chambers were prepared using 300 mm 200 gauge layflat tubing. The synthetic plastics tubing was attached to oblong stainless steel frames (150 mm by 150 mm by 900 mm) using double-sided adhesive tape. 200 mm squares of cotton netting were used to cover the ends of the chambers and were secured using adhesive tape.

Mosquitoes (naive insects of the species Aedes aegypti, 4 to 7 days old) were introduced into each chamber 8 and the chambers 8 were kept in a separate room until the test was ready to begin.

The exhaust fan which vents the room in which the test was performed was switched on.

Four targets 5 (only two shown) were prepared as follows: double layers of semi-porous membrane were stretched over the open ends of four open ended glassware bulbs (diameter of open end 43 mm) and secured using elastic bands. Testing was carried out at 27° C. The membranes were kept moist and warmed above the ambient temperature throughout the test by passing a supply of water (at 340° C.) through the glassware bulbs, so as to contact the inner surface of the membranes.

Menthyl 2-pyrrolidone-5-carboxylate (30 microlitres) was applied to a membrane and spread as evenly as possible across the membrane surface. This was repeated with two other membranes and the fourth membrane was left untreated as a control.

The chambers 8 containing the mosquitoes were positioned so that each chamber had one netting end pressed against one of the targets 5. Glass partitions in the form of a cross 6 were used to separate each target 5 and chamber end from its neighbour.

600 mm 200 gauge layflat tubing was used to connect the various elements as shown in FIG. 1, air was forced by an inlet fan (not shown) over the filters 2, 3, over the targets 5 and through the test chambers containing the mosquitoes. The separation of the membranes ensured that air passing over a particular membrane would pass through only one test chamber 8.

The filters 2, 3 were used to remove volatile elements from the air passing over the mosquitoes; filter 2 contained activated charcoal and filter 3 contained a molecular sieve (Union Carbide type 5A zeolite). The material in each filter 2, 3 was held within the cells of a 25 mm thick sheet of aluminium honeycomb sandwiched between two sheets of stainless steel mesh held in an aluminium frame. The filters 2,3 were bolted by their frames to the inside of an aluminium tunnel such that air passing along the tunnel passed through the filters 2, 3.

Four cameras 9 (only two shown) positioned downwind of the test chambers 8 were each focused onto a particular target 5, and the images produced by the cameras displayed on a single monitor 15 by means of a quad splitter 13. An electronic timer was used to project the date and time onto the screen, and the video recorder 14 was used to record the data.

The mosquitoes in the test chambers 8 were activated by introduction of a human breath stimulus upwind of the targets 5 and the number of insects attempting to bite each target 5 over the next ten minute period was recorded. After ten minutes, the recording was stopped and the test chambers 8 removed from their position immediately downwind of the targets 5.

The targets 5 were left untouched (although still warmed and moistened) for one hour with the fans switched on, after which time the test chambers 8 were re-introduced and the test repeated to determine the repellency of the menthyl 2-pyrrolidone-5-carboxylate one hour after application.

The numbers of mosquitoes attempting to bite each of the targets 5 was noted every 10 seconds throughout each ten minute recording period. The 60 readings were used to produce a figure for the mean number of insects biting each target 5 during the ten minute test periods. The reading obtained for the untreated target 5 was used to give a measure of the basic avidity of the mosquitoes used in the test and this was taken into account when analysing the results.

The standard insect repellent N,N-diethyl-m-toluamide (DEET) and menthol, one of the hydrolysis products of menthyl 2-pyrrolidone-5-carboxylate, were also tested using the same apparatus for comparison with menthyl 2-pyrrolidone-5-carboxylate The results are given in Table 1 below.

TABLE 1

| Compound | % Repellency | |
| --- | --- | --- |
| | initially | After 1 Hour |
| Menthyl 2-pyrrolidone-5-carboxylate | 80 | 59 |
| DEET | 93 | 75 |
| Menthol | 49 | 25 |

EXAMPLE 2

Compositions suitable for use in the invention include the following:

A. Dry Oil Sprays

| | 1<br>% by weight | 2<br>% by weight |
|---|---|---|
| PERFUME | 20.00 | 14.60 |
| CERAPHYL 375 | 18.00 | 14.60 |
| ETHANOL | 10.00 | — |
| PERMETHYL 99A | 50.00 | 68.80 |
| MENTHYL 2-PYRROLIDONE-5-CARBOXYLATE (QUESTICE) | 2.00 | 2.00 |

The menthyl 2-pyrrolidone-5-carboxylate was dissolved in the ethanol or permethyl and other ingredients were added with stirring.

B. Body Lotion

| | | % by weight |
|---|---|---|
| PURIFIED WATER (a) | | to 100.00 |
| AMERGHOL L101 | Mineral Oil & Lanolin Alcohol | 8.50 |
| DOW CORNING 1401 | Cyclomethicone & Dimethiconol | 4.00 |
| QUESTICE L | Menthyl 2-pyrrolidone-5-carboxylate | 1.50 |
| ESTOL GMS (S/E) 1461 | Glyceryl Stearate SE | 1.50 |
| STEARIC ACID | | 1.50 |
| D-PANTHENOL 75L | | 1.00 |
| TRIETHANOLAMINE | | 0.60 |
| PEMULEN TR1 | Acrylates/C10–30 Alkyl Acrylate Crosspolymer | 0.30 |
| DOW CORNING 200/350 | Dimethicone | 0.20 |
| NIPAGIN M | Methylparaben | 0.20 |
| NIPASOL M | Propylparaben | 0.15 |
| GERMALL 115 | Imidazotidinyl Urea | 0.15 |
| PURIFIED WATER (b) | | 5.00 |
| ALLANTOIN | | 0.10 |
| PERFUME | | q.s. |

The Panthenot, Allantoin, Questice L were blended until the mixture was smooth and clear. The water and Nipagin were added and the mixture (water phase) was heated to 75° C. The Amerchol, Estol GMS, stearic acid, Dow Corning 200/350 and Nipasol were combined and heated to 75° C. The Pemulen was added to this mixture, ensuring that the temperature did not rise above 85° C., to form a slurry. The slurry was added to the 10 water phase and the resultant mixture was homogenised with addition of the triethanolamine until the product was smooth and lump-free. After cooling to 40° C with stirring, the Dow Corning 1401, Germall and water (b) were added and mixed in thoroughly.

C. Moisturiser

| | | % by weight |
|---|---|---|
| PURIFIED WATER | | to 100.00 |
| FLORASUN 90 | Sunflower Seed oil | 10.00 |
| BUTYLENE GLYCOL | | 4.00 |
| SEPIGEL 305 | Polyacrylamide & C13–14 Isoparaffin & Laureth-7 | 1.60 |
| ARLACEL 165 | Glyceryl Stearate & PEG-100 Stearate | 2.50 |
| ILLIPE BUTTER | | 2.00 |
| DRY-FLO PLUS | Aluminium Starch Octenylsuccinate | 2.00 |

C. Moisturiser -continued

| | | % by weight |
|---|---|---|
| QUESTICE L | Menthyl 2-pyrrolidone-5-carboxylate | 1.70 |
| FLORAESTERS-20 | Jojoba Oil & Jojoba Wax | 1.00 |
| FLORAESTERS-30 | Jojoba Oil & Jojoba Wax | 1.00 |
| PARSOL MCX | Octyl Methoxycinnamate | 1.00 |
| PONGAMIA EXTRACT | Pongamol | 1.00 |
| SPAN 60 | Sorbitan Stearate | 0.50 |
| VITAMIN E ACETATE | | 0.50 |
| D-PANTHENOL | | 0.50 |
| PHENONIP | Phenoxyethanol & Methylparaben & Ethylparaben & Propylparaben & Butylparaben | 0.40 |
| NERVANAID BA2 | Disodium EDTA | 0.10 |
| PERFUME | | q.s. |

The water and Nervanaid were combined and heated to 75° C. (main batch). Separately the illipe butter, Floraesters, Florasun, Arlacel, Span, PONGAMIA EXTRACT and QUESTICE L were combined and heated to 75° C. The oils were added to the main batch with stirring, which was then cooled to 60° C. and the Sepigel was added, homogenising until smooth and thick. After cooling to 45° C., the Butylene Glycol and Dry-Flo were combined to make a slurry, and added to the main batch. After cooling to room temperature, the remaining ingredients were added.

D. Foot Cream

| | | % by weight |
|---|---|---|
| PURIFIED WATER | | to 100.00 |
| CETYL ALCOHOL | | 3.00 |
| SQUALENE | | 2.50 |
| EMPILAN KM 20 | Ceteareth 20 | 2.60 |
| LIQUIWAX DIEFA | Diisoarachidyl Dilinoleate | 2.50 |
| SEPIGEL 305 | Polyacrylamide & C13–14 Iso-paraffin & Laureth-7 | 2.00 |
| QUESTICE | Menthyl 2-pyrrolidone-5-carboxylate | 1.50 |
| DOW CORNING 200/350 | Dimethicone | 0.80 |
| NIPAGIN M | Methylparaben | 0.20 |
| NIPASOL M | Propylparaben | 0.15 |
| GERMALL 115 | Imidazolidinyl Urea | 0.15 |
| PERFUME | | q.s. |

The water, Nipagin and Sepigel were combined and heated to 75° C. The oils were combined, heated to 75° C. and added to the water phase with homogenising. The resultant mixture was cooled to room temperature with occasional stirring. The Germall was mixed with a little water, stirred until clear and added to the main batch.

E. Liquid Talc

| | | % by weight |
|---|---|---|
| PURIFIED WATER | | to 100.00 |
| QUESTICE L | Menthyl 2-pyrrolidone-5-carboxylate | 2.00 |
| DOW CORNING 1401 | Cyclomethicone & Dimethiconol | 2.00 |
| TALC | | 2.00 |

-continued

E. Liquid Talc

| | | % by weight |
|---|---|---|
| POLAWAX GP200 | Cetearyl Alcohol & PEG-20 Stearate | 1.50 |
| ESTOL GTCC 3603 | Capric/Caprylic Triglyceride | 1.50 |
| DRY-FLO PLUS | Aluminium Starch Octenyl-succinate | 1.00 |
| CETEARYL ALCOHOL | Lanette O | 0.60 |
| TRIETHANOLAMINE | | 0.50 |
| CARBOPOL ULTREZ 10 | Carbomer | 0.20 |
| SILKALL 100 | Silk | 0.20 |
| EUXYL K400 | Methyldibromo Glutaronitrile & Phenoxyethanol | 0.20 |
| PERFUME | | q.s. |

The Estol was added to the water, then the Carbopol was sprinkled on and allowed to wet out. The resultant mixture was heated to 65° C. The Cetearyl Alcohol, Polawax and Questice L were combined and heated to 65° C. and added to the water phase with shear. While homogenisation continued the remaining ingredients were added, except the Euxyl, which was added cold.

F. Moisturising Gel

| PHASE | INCI NAME | TRADE NAME | % by weight |
|---|---|---|---|
| A | Ceteareth-20 | Empilan KM20 | 2.00 |
| | Menthyl 2-pyrrolidone-5-carboxylate | QUESTICE L | 0.75 |
| | QUEST PERFUME | AF 26689 | 0.20 |
| | Ethanol | | 10.00 |
| | Water (a) | | 10.00 |
| | PEG-25 PABA | Uvinul P25 | 3.00 |
| B | Carbomer (1% Soln.) | Carbopol 940 | 50.00 |
| | Water (b) | | to 100.00 |
| | Imidazolidinyl Urea | Germall 115 | 0.20 |
| | Patent Blue V | Blue V (0.5% Soln.) | 0.10 |
| | Panthenol | D-Panthenol 751 | 0.75 |
| | Sodium Hyaluronate | | 0.50 |
| C | Triethanolamine | | 0.60 |

The EMPILAN, QUESTICE L, QUEST PERFUME, UVINUL and ETHANOL were mixed together and once the mixture was homogenous, the WATER (a) was added. A solution of CARBOPOL was prepared and combined, in the main vessel, with WATER (b) and the remaining ingredients of phase B. To this gel, was added phase A in portions, mixing slowly but thoroughly between each addition.

EXAMPLE 3

An insect repellent lotion was prepared to the following formulation.

| | per cent by weight | | |
|---|---|---|---|
| | A | B | C |
| Phase A | | | |
| Water | to 100.00 | to 100.00 | to 100.00 |
| Glycerine | 5.00 | 5.00 | 5.00 |

-continued

| | per cent by weight | | | |
|---|---|---|---|---|
| | | A | B | C |
| Phase B | | | | |
| Dehyquart DAM | (i) | 6.50 | 6.50 | 6.50 |
| Petroleum Jelly | (ii) | 7.00 | 7.00 | 7.00 |
| DEET | (iii) | 10.00 | 0.00 | 8.00 |
| Crodamol IPP | (iv) | 5.00 | 5.00 | 5.00 |
| Cetyl Alcohol | | 3.00 | 3.00 | 3.00 |
| Dow Corning 200/350 | (v) | 1.00 | 1.00 | 1.00 |
| Questice ™ L | (vi) | 0.00 | 2.00 | 2.00 |
| Phase C | | | | |
| Phenonip | (vii) | 0.60 | 0.60 | 0.60 |

INCI Names
(i) Distearyl dimethyl ammonium chloride
(ii) Petrolatum
(iii) Diethyl toluamide
(iv) Isopropyl palmitate
(v) Dimethicone
(vi) Menthyl PCA [2-pyrrolidone-5-carboxylate]
(vii) Phenoxtethanol Phases A and B were separately heated to 70° C. and A was slowly added to B with shearing. The mixture was stirred until cool, then sheared again until completely homogenous. Finally Phase C was added with stirring.

The above lotions were tested for insect repellency using the method outlined in Example 1. The results are given below in Table 2.

TABLE 2

| | % Repellency | |
|---|---|---|
| | Initial | After 1 hour |
| Cream A | 96 | 87 |
| Cream B | 64 | 44 |
| Cream C | 92 | 69 |

What is claimed is:

1. A method of repelling insects from an object or airspace comprising applying to the object or into the airspace an effective amount of menthyl 2-pyrrolidone-5-carboxylate.

2. The method of claim 1 wherein the menthyl 2-pyrrolidone-5-carboxylate is applied to the object or into the airspace as a perfumed composition.

3. The method of claim 1 wherein the menthyl 2-pyrrolidone-5-carboxylate is applied as a composition which contains at least 0.05% by weight of menthyl-2-pyrrolidone-5-carboxylate.

4. The method of claim 3 wherein said composition comprises a personal product, a cosmetic or a household product.

5. The method of claim 4 wherein said composition comprises a fine fragrance, a cologne, a skin cream, a skin lotion, a deodorant, a talc, a bath oil, a soap, a shampoo, a hair conditioner, a styling agent, an air freshener, a hard surface cleaner or a laundry product.

6. The method of claim 2 wherein the composition comprises between 0.1% and 10% by weight of a personal product, cosmetic or household product.

7. The method of claim 1 wherein the insects are mosquitoes.

8. A method of repelling insects which comprises exposing said insects to an effective repelling amount of menthyl 2-pyrrolidone-5-carboxylate.

9. A composition for use as an insect repellent which comprises a mixture of menthyl-2-pyrrolidone-5-carboxylate and an insect repellent selected from the group consisting of N,N-diethyl-m-toluamide (DEET), N,N-diethylbenzamide, citronella, Tolu balsam, Peru balsam, Eucalyptus oil, Huon pine oil, camphor, cypress oil, galbanum, diethyl phthalate, dimethyl phthalate, dibutyl phthalate, 1,2,3a,4,5,5a,6,7,8,9,9b-dodecahydro-3a,6,6,9a-tetramethyl-naphtho[2,1-b]furan, 4-(tricyclo[$5.2.1.0^{2,6}$]decylidine-8)butanal, 1-ethoxy-1-(2'-phenylethoxy)ethane, acetyl cedrene and propylidene phthalide.

10. A composition for use as an insect repellent comprising a mixture of menthyl 2-pyrrolidone-5-carboxylate and a second compound, said second compound having a repellency of at least 20%.

11. A composition, according to claim 10 in which said second compound has a repellency of at least 40%.

12. A composition according to claim 10 or 11 in which said second compound has a repellency of at least 50%.

13. A composition for use as an insect repellent comprising a mixture of menthyl 2-pyrrolidone-5-carboxylate and a second compound, said second compound being present in an amount which is sufficient to ensure that said second compound contributes to said composition an insect repellent effect equivalent to a repellency of at least 10%.

14. A composition according to claim 13 in which the amount of said second compound is sufficient to ensure that said second compound contributes to said composition an insect repellent effect equivalent to a repellency of at least 20%.

15. A composition according to claim 13 or 14 in which the amount of said second compound is sufficient to ensure that said second compound contributes to said composition an insect repellent effect equivalent to a repellency of at least 30%.

* * * * *